United States Patent [19]
DerVartanian et al.

[11] Patent Number: 6,020,204
[45] Date of Patent: Feb. 1, 2000

[54] RAPID AND ACCURATE COLORIMETRIC DETERMINATION OF NICKEL AND COBALT IN PROTEIN SOLUTIONS

[75] Inventors: Daniel V. DerVartanian; Matthew R. Chenoweth, both of Athens, Ga.

[73] Assignee: University of Georgia Research Foundation, Inc., Athens, Ga.

[21] Appl. No.: 09/082,315

[22] Filed: May 20, 1998

[51] Int. Cl.$^7$ .......................... G01N 33/20; G01N 21/78
[52] U.S. Cl. ................ 436/74; 436/166; 436/84
[58] Field of Search .............................. 436/73, 74, 84, 436/166

[56] References Cited

U.S. PATENT DOCUMENTS 5,925,570  7/1999  Nishidate et al. ........................ 436/84

FOREIGN PATENT DOCUMENTS 1451593  1/1989  U.S.S.R. .................................. 436/84

OTHER PUBLICATIONS

"Colorimetric and Spectrophotometric Analysis", Textbook of *Quantitative Inorganic Analysis*, pp. 794–795, Vogel 1961.
S. E. Allen, *Chemical Analysis of Ecological Materials*, pp. 327–329, (1974).
F. W. Sunderman, Jr., "Analytical Biochemistry of Nickel", Pure and Applied Chemistry, V 52, pp. 529–544 (1980).
"A highly sensitive extraction–photometric method for nickel with dithizone and phenanthroline", Talanta, vol. 16, pp. 412–414 (1969).
A.K. Majumdar, et al., "Chromotropic Acid Azo Dyes of the Pyridine Series", Talanta, vol. 13, pp. 821–828 (1966).
C.G. Perez, et al., "Spectrophotometric Determination of Nickel by Oxidation of the Nickel (II)—Nioxime Complex with Hexacyanofei Rate (III) in Sodium Hydroxide Medium", Analytica Chimica Acta. 87, pp. 233–237 (1976).
P. Koch, et al., "The Nickel–Catalysed Carbonylation of 2–Mercaptoethanol", Journal of Organometallic Chemistry, 81, pp. 111–114 (1974).
B. S. Snyder, et al., Mono–and Bi–nuclear Metal (II) Complexes of Ethane–1, 2–dithiolate: Preparation, Equilibrium and Redox Properties of $[Ni(S_2C_2H_4)_2]^{2-}$—and $[Ni(S_2C_2H_4)_3]^{2-}$, and the Structures of $Ni_2(S_2C_2H_4)_3{}^{2-}$ and $[Pd(S_2C_2H_4)_2]^{2-}$—Aust J. Chem, 39, pp. 963–974 (1986).
S.K. Argra, et al., "The Ethylammonium Salt of the Nickel (II) Complex of Ethyldithiophosphonic Acid", Acta Cryst., B34, pp. 3355–3357 (1978).

M.W. Grant, et al., "The Lewis–Acidity of Square–Planar Nickel (II) Complexes. I A Kinetic and Thermodynamic Study of the Reaction of Bis(O,O–diethyl phosphorodithioato–S,S'–)nickel(II) with bidentate Nitrogen Donors", Aust. J. Chem., 29, pp. 749–758 (1976).
R.W. Burke, et al., "Procedures for the Determination of Arsenic, Copper, and Nickle by Molecular Absorption Spectrometry", Section V, Molecular Absorption Spectrometry, pp. 73–84.
"Nickel: Inorganic & Coordination Chemistry", Encylopedia of Inorganic Chemistry, vol. 5, pp. 2393–2395 & 2404–2405 (1994).
"Chapter 5: General Aspects of Trace Element Analysis", *Trace Element Analysis*, Vlado Valkovic, 1975, pp. 115–117.
H. Onishi, "Photomoetric Determination of Traces of Metals Part II B", Chemical Analysis, vol. III, pp. 122–150 (1989).
E.W. Abel, et al., "Cyclic Hexameric Mercaptides of Nickel", Journal of the Chemical Society, Sec. A, pp. 1377–1378 (1966).
G.A. Barclay et al., "Sulphur–Bridged Complexes Involving the Ligand 2,2'–Dimercaptodiethyl Sulphide", Aust. J. Chem., 21, pp. 2669–2674 (1968).
C. Watters, "A One–Step Biuret Assay for Protein the Presence of Detergent", Analytical Biochemistry, pp. 695–698 (1978).
R.E. Beyer, "A Rapid Biuret Assay for Protein of Whole Fatty Tissues", Analytical Biochemistry, 129, pp. 483–485 (1983).
M.W. Scoggins, "Ultraviolet Spectrophotometric Determination of Nickel", Analytical Chemistry, 42, No. 2, pp. 301–303 (1970).
D.P. Ambhore, et al., "Simultaneous Determination of Cobalt & Nickel with 3–thiobenzoyl–1–p–tolythiocarbamide", Indian Journal of Chemistry, vol. 25A, pp. 699–700 (Jul. 1986).

*Primary Examiner*—Robert J. Warden, Sr.
*Assistant Examiner*—Theresa T. Snider
*Attorney, Agent, or Firm*—Flehr Hohbach Test Albritton & Herbert

[57] ABSTRACT

An inventive method and reagent for the colorimetric determination of nickel and cobalt is provided. The method and reagent uses dithiothreitol and a phosphate buffer to quantitatively detect nickel and cobalt at 465 nm and 485 nm, respectively. The method and reagent are accurate over a nickel concentration range of 1.76 to 35.2 ppm, and over a cobalt concentration range of 0.587 to 17.6 ppm. The invention is valid in protein solutions, requires no extractions and uses stable reagents. Common metals found in biological system do not interfere with the method.

10 Claims, 6 Drawing Sheets

ABSORPTION SPECTRUM OF 0.1 mM Ni IN 50 mM $PO_4$ AND 10 mM DTT.

FIG. 1

EFFECTS OF PHOSPHATE CONCENTRATION
ON ABSORBANCE AT 1mM DTT.

FIG. 2

EFFECTS OF DTT CONCENTRATION ON
ABSORBANCE AT 10 mM $PO_4$.

FIG. 3

TIME DEPENDENCE AT 50 mM $PO_4$ AND 10mM DTT.

FIG. 4

ABSORPTION SPECTRUM OF 0.1 mM
COBALT IN 50 mM $PO_4$ AND 10 mM DTT.

FIG. 5

POSSIBLE SOURCES OF INTERFERENCE.

FIG. 6

RAPID AND ACCURATE COLORIMETRIC DETERMINATION OF NICKEL AND COBALT IN PROTEIN SOLUTIONS

FIELD OF THE INVENTION

The present invention relates generally to a method and reagent for colorimetric determination of nickel and cobalt, and more specifically to a method and reagent using dithiothreitol and a phosphate buffer to quantitatively detect nickel and cobalt.

BACKGROUND OF THE INVENTION

Determination of certain metals is of value in a variety of industries. Quantitative determinations of metals plays a role in commercial industries as well as in environmental studies. Two such metals of interest are nickel and cobalt. It is particularly useful to quantitatively determine the presence of nickel and cobalt in protein solutions, such as in biological materials.

There are many determination methods reported in the prior art. One commonly used method is to detect nickel by colorimetric means, such as where a nickel sample is analyzed by spectroscopy. The most well known and widely used colorimetric method of determining nickel is the dimethylglyoxime test. This test has been used for many years, however, it has major drawbacks. The test is time consuming and inconvenient, and excess reagent may precipitate thereby adversely affecting the results of the test. Moreover, many metal ions interfere with this procedure, and a series of chloroform extractions, followed by ammonia and hydrochloric acid washes are necessary to remove the metal ions and prevent interference.

Another method for colorimetric, or spectrophotometric, determination of nickel in biological materials uses α-furildioxime as the reagent. This method differs from the dimethylglyoxime procedure only in the reagent used; this test has all the problems of the aforementioned method, and is only useful over a very narrow concentration range of nickel (0.5 to 4.0 ppm nickel).

Many other methods for the colorimetric determination of nickel are reported, however all of these methods exhibit significant limitations. Some are excessively slow or overly narrow. Others require hazardous solvents or involve reagents which must be synthesized in the laboratory. Some methods measure wavelength in the ultraviolet range where common detergents may cause interference. And further, many techniques require very large sample sizes of up to 200 ml and rely on preconcentration techniques to achieve their sensitivity.

Another limitation of prior art methods, is their susceptibility to interference from other metals. The presence of other metal ions, especially cobalt, interfere with the determination of nickel. Extraction techniques are required to remove the interference, and some techniques are quite elaborate such as using anion exchange chromatography to remove interference from cobalt, copper and iron as described by Scoggins, M. W., *Analytical Chemistry*, v. 42, p 301–3.

It is known that nickel forms colored compounds when reacted with certain thiolates. For example, dithizone has been used to determine nickel by colorimetric means. However, this method requires extraction techniques using chloroform which make this process no better than the other prior art techniques. Another thiolate compound, namely 3-thiobenzoyl-1-p-tolylthiocarbamide, has been reported as a reagent for colorimetric determination of both nickel and cobalt in Ambhore, D. P. and Joshi, A. P., *Indian Journal of Chemistry*, v. 25, p 699–700; but again, this technique requires extractions and the thio compound must be synthesized in the laboratory.

Thus, it is highly desirable to provide a method and reagent capable of providing a rapid and accurate determination of nickel and cobalt, that operates over a wide range of concentrations, is not suspectable to interference from other metal ions and is free from cumbersome extraction techniques.

OBJECTS AND SUMMARY OF THE INVENTION

Accordingly, it is an object of the present invention to provide an improved method and reagent for the colorimetric determination of nickel and cobalt.

More specifically, it is an object of the present invention to provide a method and reagent using dithiothreitol in a phosphate buffer to quantitatively detect nickel and cobalt.

A further object of the present invention is to provide a method and reagent that accurately detects nickel and cobalt over a wide range of concentrations, and additionally is accurate for detecting nickel and cobalt present in protein solutions.

Another object of the present invention is to provide a method and reagent that does not require extraction techniques, and is not susceptible to interference from certain metal ions.

A related object of the present invention is to provide a method and reagent that is rapid, convenient, and uses chemicals that are readily available and non-toxic.

The inventors have discovered that in combination, phosphate and dithiothreitol react to form ligands which can react with nickel or cobalt to form spectrophotometrically detectable nickel or cobalt phosphothiocomplexes. The discovery that nickel and cobalt react with phosphate and dithiothreitol to form these calorimetric compounds was completely unexpected. The invention provides a method of determining nickel and cobalt, comprising the steps of: preparing a reagent comprising a solution of dithiothreitol and a phosphate buffer, wherein the phosphate buffer has a pH in the range of approximately 7.5 to 9.0. The reagent is mixed with a sample containing nickel or cobalt and then the presence of nickel or cobalt is detected by colorimetric means. Alternatively, the method and reagent of the present invention provides for determination of nickel and cobalt when present in the same solution under certain conditions (discussed below).

In an alternative embodiment of the invention, a reagent for determining the presence of nickel and cobalt is provided comprising a solution of dithiothreitol and phosphate buffer, the phosphate buffer having a pH in the range of approximately 7.5 to 9.0.

BRIEF DESCRIPTION OF THE FIGURES

Other objects and advantages of the invention become apparent upon reading of the detailed description of the invention provided below and upon reference to the drawings in which.

DETAILED DESCRIPTION OF THE INVENTION

A method and reagent for calorimetric determination of nickel and cobalt is described. Unless indicated otherwise, the various materials, concentrations, and the like specified herein are illustrative only and are not to be construed as limiting the scope of the invention. The inventors have discovered that the combination of phosphate and dithiothreitol create a reagent that will react with nickel and cobalt to form nickel and cobalt phosphothiocomplexes. These phosphothiocomplexes are colored, and are detectable by colorimetric means, such as with a spectrophotometer. This discovery that nickel and cobalt react with phosphate and dithiothreitol to form calorimetric compounds is a completely unexpected result.

In accordance with the present invention, the reagent is comprised of a solution of phosphate buffer and dithiothreitol (DTT). Both of these components of the reagent are commercially available biochemicals which are stable and inexpensive. In one embodiment, sodium phosphate buffer, specifically $Na_2HPO_4$ is used. The sodium phosphate buffer is added in an amount suited to adjust the pH of the reagent to be at least slightly alkaline. Preferably the pH of the reagent is in the range of approximately 7.5 to 9.0, with a pH of 7.5 being most preferred.

According to the present invention the reagent solution may be prepared in a variety of concentrations, and it has been found that certain concentrations are best suited for certain applications. In general, the reagent is prepared as a solution of phosphate buffer and DTT where the concentration of phosphate buffer in the solution is in the range of approximately 0.1 mM to 100.0 mM phosphate buffer. The concentration of DTT in the reagent is in the range of approximately 0.1 mM to 10.0 mM DTT. The preferred concentration of the reagent will depend upon the composition of the nickel and cobalt sample to be tested. When the nickel or cobalt samples do not contain proteins, the reagent solution preferably has a concentration of 10 mM phosphate buffer and 1 mM DDT. It has been found however, that when nickel and cobalt are present in a protein solution, that different reagent solution concentrations are preferred. Specifically, when nickel or cobalt are present in protein solutions, the preferred concentration of the reagent solution is 50 mM phosphate buffer and 10 mM DTT. Additionally, nickel and cobalt present in the same solution can be determined by the present invention under the following conditions: if nickel is present at ten times the concentration of cobalt, nickel can be determined with an error of approximately 10%. Conversely, if cobalt is present at 10 times the concentration of nickel, cobalt can be determined when an approximate error of 10%. At higher concentrations, either nickel or cobalt will interfere because of spectral overlap.

Figure 1:
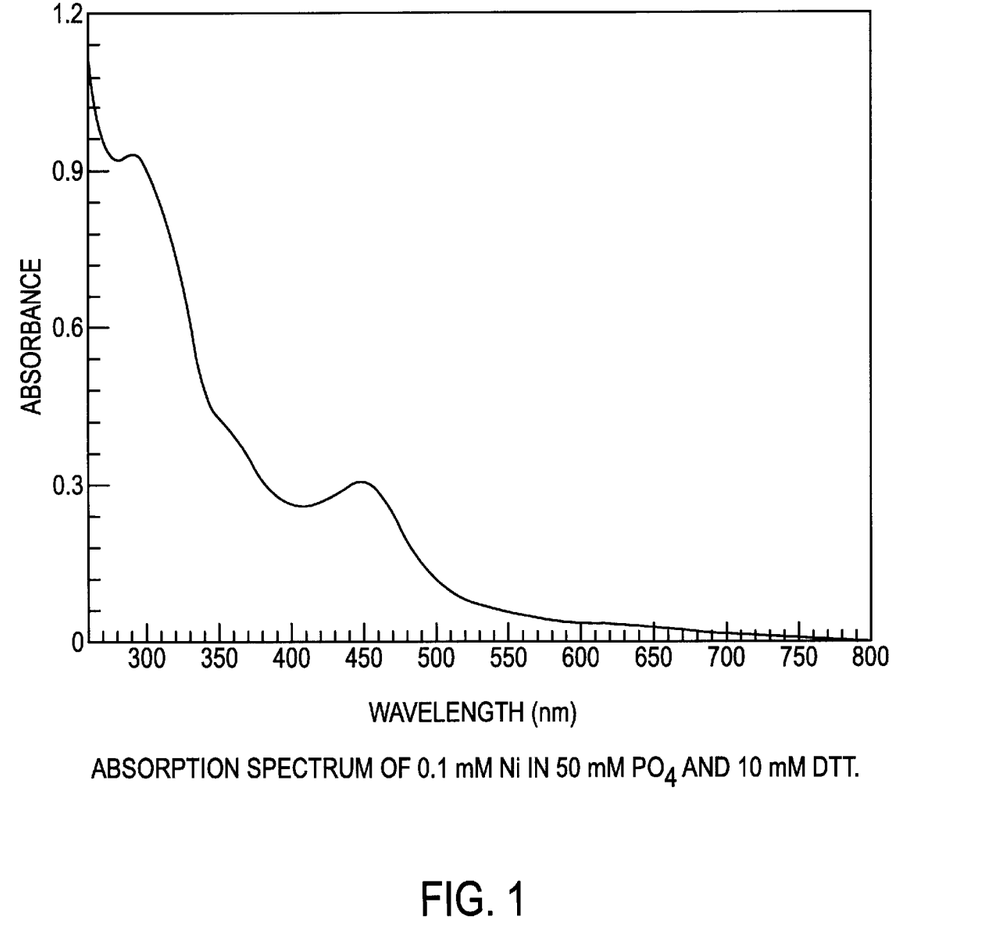
FIG. 1 shows the absorption spectrum of nickel in a reagent according to one embodiment of the present invention.

Of particular advantage, the method and reagent of the present invention is easily practiced. In an exemplary embodiment, aliquots of 1.0 ml were prepared containing nickel samples ranging in concentration from 0.587 to 35.2 ppm nickel. Each aliquot was added to a cuvet, followed by the addition of 0.1 ml of 0.1 M $Na_2HPO_4$ at a pH of 7.5. Then 0.1 ml of 0.01 M dithiothreitol was added. The cuvets were inverted to mix the reagents. The samples were then let set for up to ten minutes to allow the nickel phosphothiocomplexes to form and the color to develop. The addition of DTT to the nickel sample and phosphate solution yields a red-brown compound. The nickel sample was then tested by colorimetric means, in this case spectroscopy was used. Specifically, the samples were placed in a Varian DMS 90 spectrophotometer with a Hewlett Packard 7015B X-Y recorder with 1.0 cm quartz cells and UV-visible measurements were made. Absorbance at a wavelength of 462 nm was measured. FIG. 1 shows the absorption spectrum for nickel using a 0.1 mM sample of nickel in a reagent of 50 mM phosphate buffer and 10 mM DTT.

In another embodiment, nickel samples contained in protein solutions were tested. Since proteins are present, higher concentrations of reagent components are preferred. In an exemplary embodiment, aliquots containing protein solutions (at a final concentration of 2 mg per ml) were prepared. Nickel was added in concentrations of 0.587 to 29.4 ppm. Each aliquot was added to a cuvet, followed by the addition of 50 mM $Na_2HPO_4$ at a pH of 7.5. Thereafter, 10 mM dithiothreitol was added. The cuvets were inverted to mix the reagents. Again, the samples were then let set for up to ten minutes to allow the color to develop, and absorbance measurements at 462 nm were made. After approximately twenty tests, the cuvets must be soaked in a 30% $HNO_3$ solution for ninety minutes to remove the colored deposits on the inner walls.

Figure 2:
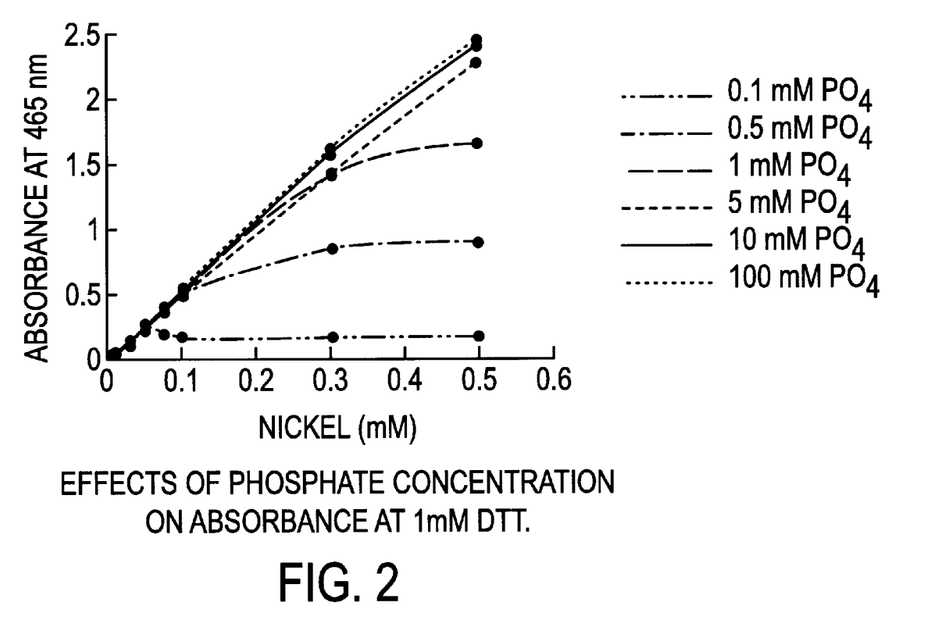
FIG. 2 illustrates the effects on the absorbance of nickel at a wavelength of 465 nm, using a reagent of varying phosphate concentration and constant DTT concentration in accordance with the present invention.
Figure 3:
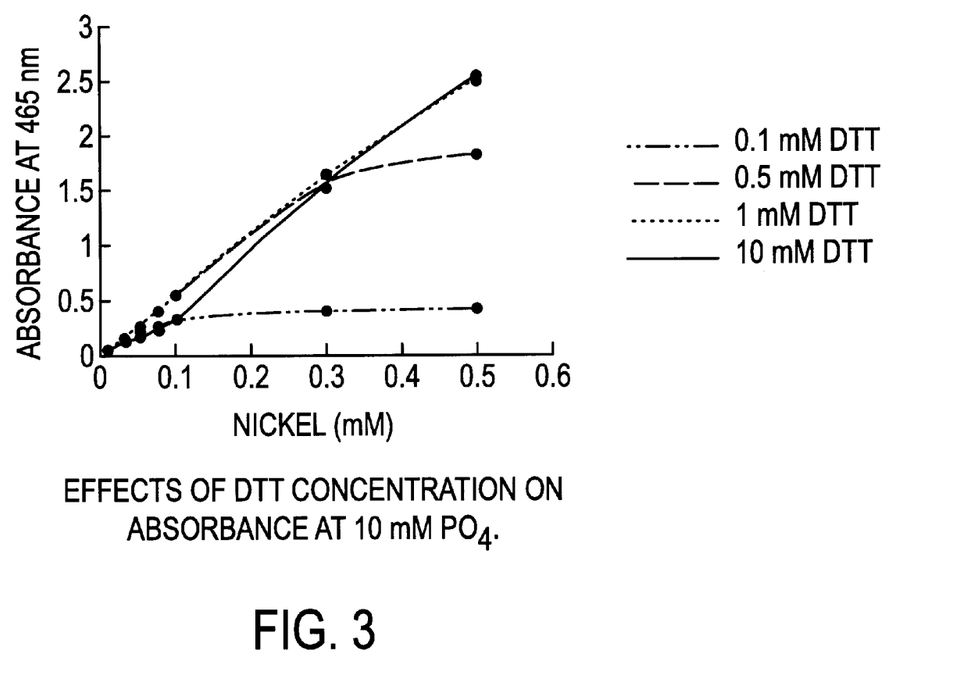
FIG. 3 shows the effects on the absorbance of nickel at a wavelength of 465 nm, using a reagent of varying DTT concentration and constant phosphate concentration in accordance with the present invention.

To determine the optimum range of the reagent concentration, the absorbance as a function of varying phosphate and DDT concentrations for different nickel samples was tested and is shown in FIGS. 2 and 3, respectively. Referring to FIG. 2, the concentration of phosphate was tested at the following concentrations: 0.1 mM, 0.5 mM, 1.0 mM, 5 mM, 10 mM, and 100 mM (these concentrations are the final concentrations of the reactants). Absorbance measurements at 465 nm were taken at the various phosphate concentrations for different nickel samples. The DTT concentration of the reagent was held constant at 1 mM DTT. The results are illustrated in FIG. 2.

Referring to FIG. 3, the DTT concentration was varied and absorbance measurements were taken at 465 nm for the same nickel samples. In this case the DDT concentrations tested were: 0.1 mM, 0.5 mM, 1.0 mM, and 10 mM (these concentrations are the final concentrations of the reactants). The phosphate concentration was held constant at 10 mM. From FIGS. 2 and 3 it is determined that the maximum absorption is found when the phosphate concentration is 10 mM, and the DTT concentration is 1 mM. Additionally it is found that the absorption increases linearly over a nickel concentration range of 1.76 to 35.2 ppm.

Figure 4:
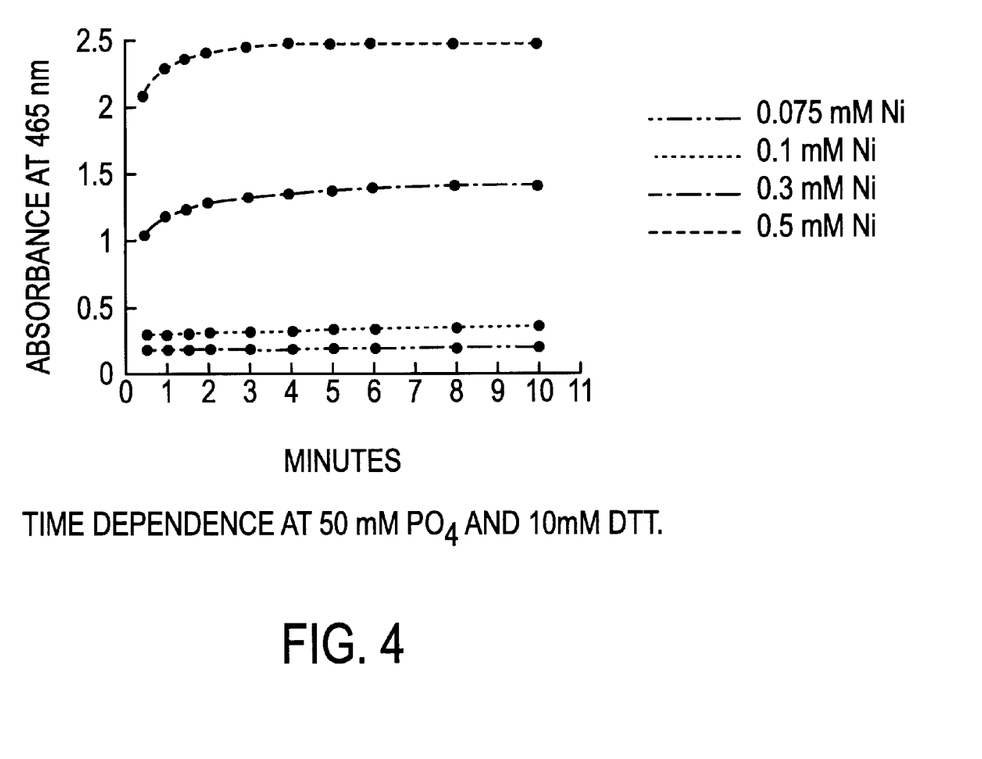
FIG. 4 depicts the time dependence of absorbance at various nickel concentrations with the reagent in accordance with one embodiment of the present invention.

The inventors have found that the timing of the reaction between the reagents and the samples plays a role in accurate detection. In FIG. 4 the time dependence of the reaction using a 50 mM phosphate and 10 mM DTT reagent as a function of differing nickel concentration is shown. Specifically, the nickel concentrations tested were: 0.075 mM, 0.1 mM, 0.3 mM and 0.5 mM. Absorbance was measured at 465 nm, and as shown the absorbance increased with time up to 10 minutes in all the nickel samples. Although not shown in FIG. 4, it was found that after 15 minutes, the color will begin to break down in samples with higher metal concentrations (i.e. ≧12 ppm) due to precipitation. In samples with lower metal concentrations (i.e. <12 ppm) the color is stable for at least thirty minutes.

For accurate determination of nickel and cobalt, careful control of the pH of the reagent solution must be considered. The phosphate buffer sets the pH of the reagent solution. The inventors have discovered that the reagent solution must have a particular pH range in order to detect nickel and cobalt. It is necessary for the reagent solution to be at least slightly alkaline for the reaction between the reagents and the samples to take place. The pH must be at least 7.5 for the reaction to proceed. When the determination was conducted using a phosphate buffer with a pH of 5.0, no color developed. Measurements with a phosphate buffer having a pH of 10.5 resulted in an absorbance value of zero. The preferred pH of the phosphate buffer is in the range of 7.5 to 9.0, with a pH of 7.5 being most preferred. Acidic or strongly basic solutions block the formation of the nickel and cobalt phosphothiocomplex colored compounds, and thus no colorimetric detection occurs.

Figure 5:
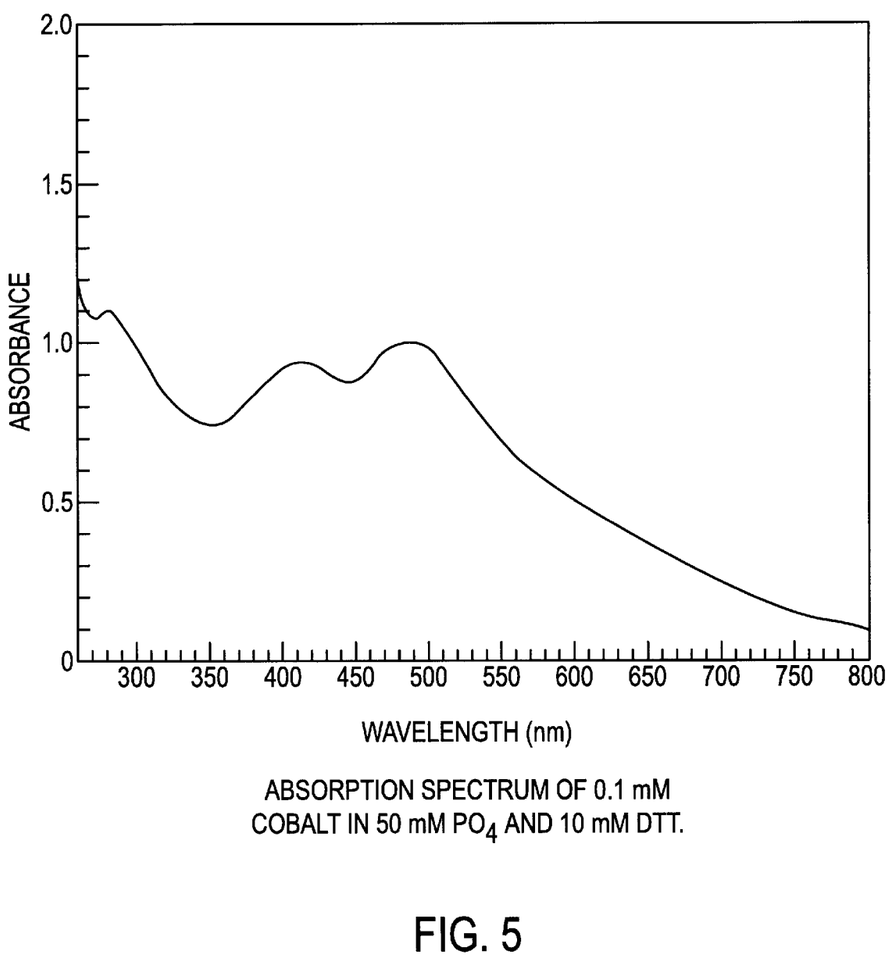
FIG. 5 shows the absorption spectrum of cobalt in the reagent according to another embodiment of the present invention.

As mentioned above, the method and reagent are also useful for determining the presence of cobalt by colorimetric means. For determining cobalt, the method and reagent are identical to that as described above for nickel. The absorption spectrum for cobalt using a 0.1 mM sample of cobalt in a reagent of 50 mM phosphate buffer and 10 mM DTT is shown in FIG. 5. Cobalt forms a cobalt phosphothiocomplex with DDT and phosphate that is a red-brown compound that absorbs more intensely than the nickel compound. As illustrated in FIG. 5 the cobalt compound has absorption maxima at 405 nm and 485 nm that are of approximately equal intensity. The absorption increases linearly over a cobalt concentration range of 0.587 to 17.6 ppm.

In aqueous solution, both nickel and cobalt exhibit significant absorbance values at concentrations of 0.587 to 35.2 ppm. Nickel obeys Beer's Law from 2.94 to 30 ppm with an absorption coefficient of 5070 L $mol^{-1}$ $cm^{-1}$ at 465 nm in a reagent of 10 mM phosphate buffer and 1 mM DTT. However, Beer's Law is not obeyed when the reagent is comprised of 50 mM phosphate buffer and 10 mM DTT.

Cobalt obeys Beer's Law under both embodiments of the above reagent compositions for cobalt samples of 1.76 to 17.6 ppm. For cobalt samples prepared in a reagent of 10 mM phosphate buffer and 1 mM DTT, the absorption coefficient is 8785 L $mol^{-1}$ $cm^{-1}$ for the 405 nm peak, and at the 485 nm peak the absorption coefficient is 8513 L $mol^{-1}$ $cm^{-1}$. For cobalt samples prepared in a reagent of 50 mM phosphate buffer and 10 mM DTT, the absorption coefficient is 9744 L $mol^{-1}$ $cm^{-1}$ for the 405 nm peak, and at the 485 nm peak the absorption coefficient is 9172 L $mol^{-1}$ $cm^{-1}$.

In the present invention, it seems that there are two species formed by the reaction between the nickel or cobalt samples, and the reagent. The species that is most prevalent appears to depend upon the DTT concentration relative to that of the metal ion. If there is excess DTT, the peaks formed on the absorption spectra are shifted to lower wavelengths. For example, in the case of nickel, the peak normally found at 462 nm is shifted to 445 nm. In cobalt samples, the peaks are shifted from 485 nm and 405 nm, to 465 nm and 390 nm, respectively. As the amount of metal ion increases, the peaks shift back to the higher wavelengths. This shift does not interfere with the determination of the metal concentration, but this may explain why Beer's Law is not obeyed over the entire range of the test.

Based on similarities in starting compounds and experimental agreement, it seems likely that the nickel compound formed by reaction with the reagent is a square planar structure. DTT is closely related to the mercaptides, which have been found to form square planar compounds with nickel as reported by Able and Crosse in the *Journal of Chemical Society Section A*. p. 1377. The red-brown color is characteristic of square planar nickel compounds, as is its solubility in water. Phosphate is a good π-acceptor and is reported to form square planar compounds with sulfur ligands, such as those found in DTT. With these ligands, polymerization may occur, and the latter phenomenon could explain the precipitation and loss of absorbance that occurs with time in samples containing high levels of nickel. These compounds may bear resemblance to the cyclic hexameric nickel mercaptides described by Abel and Crosse.

Figure 6:
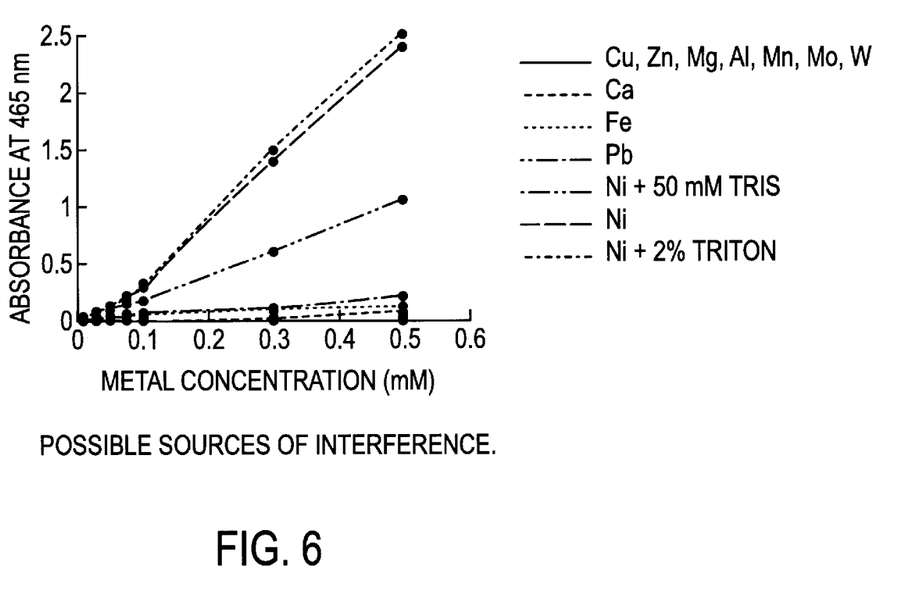
FIG. 6 illustrates possible sources of interference by plotting the effect of various constituents on absorbance as a function of their concentration.

Of significant advantage, the method and reagent of the present invention exhibit resistance to interference by other metals, unlike the prior art techniques. The effect of interference is shown in FIG. 6, a graph depicting the absorbance of nickel and a variety of metals as a function of metal concentration. There is no interference from manganese, magnesium, calcium, zinc, molybdenum, aluminum and tungsten. Most importantly, there is no interference from copper. FIG. 6 does show slight interference from iron and lead, however it is insignificant when nickel or cobalt are present in equal or greater concentrations.

It has been found that certain reagents do affect the determination method. Tris(hydroxymethyl) amninomethane ("Tris") cannot be used as a buffer solution. The presence of Tris depresses the absorbance of the nickel and cobalt compounds formed. Likewise, ethylenediaminetetracetic acid ("EDTA") cannot be added to the nickel or cobalt sample. EDTA blocks the formation of color completely, when added before the phosphate buffer and DTT. However, EDTA has no effect when added after the reaction with the reagent. t-octylphenoxypolyethoxyethanol ("Triton X-100") causes a slight increase in absorbance of nickel when present at a final concentration of 2% as shown in FIG. 6, however this is not a significant increase.

The accuracy of the dithiothreitol-phosphate method and reagent of the present invention was tested against the intercoupled plasma emission (ICP) analysis using samples containing a final concentration of 2 mg/ml proteins of various types. ICP was performed in the University of Georgia Chemical Analysis Laboratory with a Jarrell-Ash Model 96 Atomcomp. Nickel samples were tested in concentration ranges of 0.587 to 29.4 ppm. A reagent of 50 mM phosphate buffer and 10 mM DTT was added to the nickel samples. The samples were let sit for five minutes and then the absorbance was measured at 465 nm. Control blanks were prepared by substituting water for phosphate and nickel. The samples were analyzed by spectroscopy, and by ICP after the addition of $HNO_3$ to a final solution concentration of 2%.

The nickel samples were prepared with five different types of proteins: cytochrome C, carbonic anhydrase, alcohol dehydrogenase, ferritin, and apoferritin. The average error percent and standard deviation for the tests are displayed in Table 1 below:

TABLE 1

Added Nickel Only

| protein | Dithiothreitol - phosphate | | | ICP analysis | | |
|---|---|---|---|---|---|---|
| | no of test | avg error % | std dev % | no of test | avg error % | std dev % |
| cytochrome C | 34 | 6.57 | 5.79 | 22 | 18.3 | 35.3 |
| Carbonic anhydrase | 18 | 5.47 | 5.18 | 16 | 14.5 | 15.8 |
| Alcohol dehydrogenase | 18 | 9.63 | 5.32 | 17 | 16.7 | 23.2 |
| Ferritin | 15 | 9.33 | 8.67 | 12 | 8.33 | 3.91 |
| Apoferritin | 12 | 6.72 | 5.06 | 19 | 17.4 | 18.4 |

Cobalt samples were tested in concentration ranges of 0.587 to 17.6 ppm cobalt. A reagent of 50 mM phosphate buffer and 10 mM DTT was added to the cobalt samples. The samples were let sit for five minutes and then the absorbance was measured at 485 nm. Control blanks were prepared by substituting water for phosphate and cobalt. The samples were analyzed by spectroscopy, and by ICP after the addition of $HNO_3$ to final solution concentration of 2% $HNO_3$. The results are displayed in Table 2 below:

TABLE 2

Added Cobalt Only

| protein | Dithiothreitol - phosphate | | | ICP analysis | | |
|---|---|---|---|---|---|---|
| | no of test | avg error % | std dev % | no of test | avg error % | std dev % |
| Carbonic anhydrase | 24 | 4.89 | 3.77 | 18 | 13.7 | 9.66 |
| Apoferritin | 18 | 3.84 | 3.08 | 18 | 10.5 | 6.78 |
| Bovine scrum albhmin | 17 | 3.11 | 2.74 | 18 | 6.22 | 3.39 |
| Ferritin | 17 | 5.09 | 4.24 | 18 | 9.62 | 6.03 |
| Cytochrome C | 15 | 18.4 | 8.72 | 18 | 8.05 | 15.9 |

(Ni added−Ni recovered)/Ni added×100%.

In Table 2, the average error was computed by:

(Co added−Co recovered)/Co added×100%.

The standard deviation is computed by:

$$([\Sigma(x-y)^2]/n-1)^{1/2}$$

where x=the individual error, y=average error and n is the number of tests. As shown in Table 1, in 97 runs the method and reagent of the present invention gave 7.38% error, significantly better than the ICP test which returned 15.7% error in 86 tests. For cobalt, the method of the present invention exhibited 6.61% error in 91 runs. The ICP analysis returned 9.62% error in 90 runs. It is shown therefore, that the method of the present invention is superior in accuracy to plasma emission spectroscopy techniques.

Thus, an improved method of determining nickel and cobalt has been provided. The foregoing description of specific embodiments of the invention have been presented for the purpose of illustration and description. They are not intended to be exhaustive or to limit the invention to the precise forms disclosed, and obviously many modifications, embodiments, and variations are possible in light of the above teaching. It is intended that the scope of the invention be defined by the claims appended hereto and their equivalents.

We claim:

1. A method of determining nickel and cobalt comprising the steps of:

preparing a reagent comprising a solution of dithiothreitol and a phosphate buffer, said phosphate buffer having a pH in the range of approximately 7.5 to 9.0;

mixing a sample containing nickel or cobalt with said reagent, forming a colorimetric compound; and detecting the presence of nickel or cobalt by calorimetric means.

2. The method of claim 1 wherein said sample is present in a protein solution.

3. The method of claim 1 wherein the sample containing nickel has a concentration of nickel in the range of approximately 1.76 to 35.2 ppm.

4. The method of claim 1 wherein the sample containing cobalt has a concentration of cobalt in the range of approximately 0.587 to 17.6 ppm.

5. The method of claim 1 wherein said colorimetric means is spectrophototrometry.

6. The method of claim 1 wherein the solution has a final concentration of dithiothreitol in the range of approximately 0.1 mM to 10 mM when said phosphate buffer is in a final concentration in the range of approximately 0.1 mM to 50 mM.

7. The method of claim 1 wherein the pH of said phosphate buffer is approximately 7.5.

8. The method of claim 1 wherein said step of mixing further comprises waiting for a period of approximately 5 to 30 minutes before said detecting step.

9. A method of determining nickel, comprising the steps of:

preparing a reagent comprising a solution of dithiothreitol and a phosphate buffer, said phosphate buffer having a pH in the range of approximately 7.5 to 9.0, and said solution having a final concentration of dithiothreitol of approximately 10 mM and a final concentration of phosphate buffer of approximately 50 mM;

mixing a sample containing nickel in a protein solution with said reagent and forming a colorimetric compound, wherein the nickel has a concentration in the range of approximately 1.76 to 35.2 ppm in said protein solution; and detecting the presence of nickel by visible light spectrometry.

10. A method of determining cobalt, comprising the steps of:

preparing a reagent comprising a solution of dithiothreitol and a phosphate buffer, said phosphate buffer having a pH in the range of approximately 7.5 to 9.0, and said solution having a final concentration of dithiothreitol of approximately 10 mM and a final concentration of phosphate buffer of approximately 50 mM;

mixing a sample containing cobalt in a protein solution with said reagent and forming a colorimetric compound, wherein the cobalt has a concentration in the range of approximately 0.587 to 17.6 ppm in said protein solution; and detecting the presence of cobalt by visible light spectroscopy.

* * * * *